United States Patent [19]
Frigola-Constansa et al.

[11] Patent Number: 5,532,234
[45] Date of Patent: Jul. 2, 1996

[54] USE OF 1-[4-[4-ARYL (OR HETEROARYL)-1-PIPERAZINYL]-BUTYL)-1H-AZOLE DERIVATIVES FOR THE PREPARATION OF MEDICAMENTS INTENDED FOR THE TREATMENT OF DISORDERS OF GASTRIC SECRETION

[75] Inventors: Jordi Frigola-Constansa; Ramon Merce-Vidal, both of Barcelona, Spain

[73] Assignee: Laboratories Del Dr. Esteve, S.A., Barcelona, Spain

[21] Appl. No.: 344,377

[22] Filed: Nov. 23, 1994

[30]    Foreign Application Priority Data

Nov. 25, 1993 [FR] France ..................... 93 14102

[51] Int. Cl.$^6$ ..................... A61K 31/54; A61K 31/535; A61K 31/495
[52] U.S. Cl. ..................... 514/224.2; 514/233.8; 514/234.2; 514/234.5; 514/253; 514/254; 514/255; 514/925
[58] Field of Search ..................... 514/224.2, 233.8, 514/234.2, 234.5, 253, 254, 255, 925

[56]    References Cited

FOREIGN PATENT DOCUMENTS 0455510   6/1991   European Pat. Off. .

OTHER PUBLICATIONS

The Journal of Pharmacology and Experimental Therapeutics, vol. 262, No. 1, 1992, pp. 90–98–Costall et al., "Profile Of Action Of A Novel 5–Hydroxytryptamine 1A receptor Ligand E–4424 To Inhibit Aversive Behavior In The Mouse, Rat and Marmoset".

*Primary Examiner*—Kevin E. Weddington
*Attorney, Agent, or Firm*—Dressler, Goldsmith, Shore & Milnamow, Ltd.

[57]    ABSTRACT

The present invention relates to the use of 1-{4-[4-aryl(or heteroaryl)-1-piperazinyl]butyl}-1H-azole derivatives and of their physiologically acceptable salts for the manufacture of medicaments intended for the treatment of disorders associated with gastric secretion.

5 Claims, No Drawings

USE OF 1-[4-[4-ARYL (OR HETEROARYL)-1-PIPERAZINYL]-BUTYL)-1H-AZOLE DERIVATIVES FOR THE PREPARATION OF MEDICAMENTS INTENDED FOR THE TREATMENT OF DISORDERS OF GASTRIC SECRETION

The present invention relates to use of 1-{4-[4-aryl (or heteroaryl)-1-piperazinyl]butyl}-1-H-azole derivatives and of their physiologically acceptable salts for the manufacture of medicaments intended for the treatment of disorders associated with gastric secretion.

The compounds to which the present invention relates have been described in European Patents EP 382,637 and EP 497,659, as well as in European Patent EP 502,786, which relates to a process for the preparation of aryl (or heteroaryl)piperazinylbutylazole derivatives. In Patents EP 382,637 and EP 497,659, we claimed the use of these compounds in the treatment of certain diseases of the central nervous system. We have now discovered that aryl (or heteroaryl)piperazinylbutylazole derivatives show a gastric antisecretory activity and that, consequently, they are useful in the treatment of gastric hypersecretion or as anti-ulcer agents. In particular, the compounds are appropriate in preventing or treating gastrointestinal diseases in mammals, including man.

The compounds recommended in the context of the present invention correspond to the general formula I

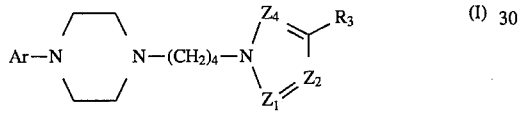

in which: Ar represents an optionally nitrogenous aromatic radical chosen from the variously substituted aryls, variously substituted 2-pyrimidine and 3-(1,2-benzisothiazole), $Z_1$ represents a nitrogen atom or an optionally substituted carbon atom which can he represented by: $C-R_1$, $Z_2$ represents a nitrogen atom or an optionally substituted carbon atom which can be represented by: $C-R_2$, $Z_4$ represents a nitrogen atom or an optionally substituted carbon atom which can he represented by: $C-R_4$, and $R_1$, $R_2$, $R_3$ and $R_4$, which are identical or different and which can also form part of another, optionally aromatic, ring, represent a hydrogen atom, a halogen, a lower alkyl radical, a nitro radical, a hydroxyl radical, an alkoxy radical, a cyano radical, a carboxyl radical, a carboxamido radical, an alkyl carboxylate radical, an aryl or substituted aryl radical, a sulfo radical, a sulfonamido radical which is optionally substituted on the amino group, or an amino or substituted amino radical.

The compounds identified by Examples 1 to 84 are obtained by the procedures described in Patents EP 382,637, EP 497,659 and EP 502,786 and the data for their identification are displayed in Table I. The following examples illustrate the properties of a few derivatives which come within the context of the present invention.

TABLE I

[Structure: pyridine-N-(CH$_2$)$_4$-N(piperazine)-N=C(R$_3$)-Z$_4$=Z$_2$-Z$_1$ ring system]

| Example | Z$_1$ | Z$_2$ | Z$_4$ | R$_3$ | M.p. | IR cm$^{-1}$ | NMR Solvent | $^1$H NMR (100 MHz), δ, J=Hz |
|---|---|---|---|---|---|---|---|---|
| 1 | CH | CH | CH | H | Oil | 2941, 1585, 1547, 1500, 1360, 1260, 983, 724 (film) | CDCl$_3$ | 1.55(m, 2H); 1.77(m, 2H); 2.25–2.55(c.a., 6H); 3.70–4.05(c.a., 6H); 6.13(t, J=2.0Hz, 1H); 6.47(t, J=4.7Hz, 1H); 6.65(t, J=2.0Hz, 2H); 8.29(d, J=4.7Hz, 2H) |
| 2 | C—CH=CH—CH=CH—C | | C—CH=CH—CH=CH— | | Oil | 2941, 1586, 1547, 1511, 1484, 1402, 1359, 1307, 1260, 983, 750, 723 (film) | CDCl$_3$ | 1.66(m, 2H); 1.86(m, 2H); 2.27–2.45(c.a., 6H); 3.78(t, J=5.2Hz, 4H); 4.30(t, J=7.1Hz, 2H); 6.43(t, J=4.7Hz, 1H); 7.12–7.46(c.a., 6H); 8.07(d, J=6.5Hz, 2H) 8.26(d, J=4.7 Hz, 2H) |
| 3 | C—CH=CH—CH=CH—C | | CH | H | Oil | 2940, 1585, 1547, 1510, 1446, 1359, 1259, 983, 741 (film) | CDCl$_3$ | 1.54(m, 2H); 1.88(m, 2H); 2.37(c.a., 6H); 3.79(t, J=5Hz, 4H); 4.13(t, J=6.8Hz, 2H); 6.45(c.a., 2H); 6.9–7.1(c.a., 5H); 8.27(d, J=4.7Hz, 2H) |
| 4 | C—CH=CH—CH=CH—C | | CPh | Ph | Oil | 2942, 1586, 1547, 1502, 1447, 1359, 1261, 984, 789, 757, 702 (film) | CDCl$_3$ | 1.38(m, 2H); 1.68(m, 2H); 2.10–2.40(c.a., 6H); 3.76(t, J=5Hz, 4H); 4.11(t, J=7Hz, 2H); 6.41(t, J=4.7Hz, 1H); 7.10–7.50(c.a., 13H); 7.79(m, 1H); 8.25(d, J=4.7Hz, 2H) |
| 5 | N | CH | CH | —C(O)NH$_2$ | 124° C. | 3337, 3156, 1663, 1601, 1586, 1446, 1360, 980 (KBr) | d$_6$-DMSO | 1.38(m, 2H); 1.81(m, 2H); 2.3–2.5(c.a., 6H); 3.69(m, 4H); 4.14(t, J=7Hz, 2H); 6.6(t, J=4.7 Hz, 1H); 7.0(broad, 1H); 7.7(broad, 1H); 7.89(s, 1H); 8.24(s, 1H); 8.35(d, J=4.6Hz, 2H) |
| 6 | N | CH | CH | —C(O)OH | 104–105° C. | 3100, 2943, 1602, 1587, 1546, 1487, 1440, 1360, 1260, 797 (film) | d$_6$-DMSO | 1.40(m, 2H); 1.81(m, 2H); 2.23–2.49(c.a., 6H); 3.0(broad, 1H); 3.64(m, 4H); 4.13(t, J=7Hz, 2H); 6.6(t, J=4.7Hz, 1H); 7.7(s, 1H); 8.1(s, 1H); 8.33(d, J=4.7Hz, 2H) |
| 7 | N | CMe | CCF$_3$ | H | 71–75° C. | 2937, 2856, 1586, 1544, 1496, 1393, 1228, 1177, 1125, 981 (KBr) | CDCl$_3$ | 1.57(m, 2H); 1.89(m, 2H); 2.30–2.55(c.a., 6H); 2.32(s, 3H); 3.82(t, J=5Hz, 4H); 4.10(t, J=7Hz, 2H); 6.25(s, 1H); 6.47(t, J=4.7Hz, 1H); 8.29(d, J=4.7, 2H) |
| 8 | CH | N | CPh | Ph | Oil | 2942, 1585, 1547, 1505, 1445, 1360, 1307, 1260, 983, 774, 734, 700 (film) | CDCl$_3$ | 1.55(m, 4H); 2.16–2.42(c.a., 6H); 3.71–3.89(c.a., 6H); 6.47(t, J=4.7Hz, 1H) 7.12–7.60(c.a., 11H); 8.27(d, J=4.7Hz, 2H) |
| 9 | CPh | N | CPh | Ph | Oil | 2942, 1585, 1546, 1501, 1445, 1360, 1260, 983, 698 (film) | CDCl$_3$ | 1.55(m, 4H); 1.95–2.33(c.a., 6H); 3.69–4.07(c.a., 6H) 6.47(t, J=4.7Hz, 1H); 7.13–7.67(c.a., 15, H); 8.26(d, J=4.7Hz, 2H) |
| 10 | CMe | N | CPh | Ph | Oil | 2942, 1585, 1547, | CDCl$_3$ | 1.43(m, 4H); 2.18–2.47(c.a., 9H); 3.72–3.76(c.a., |

TABLE I-continued

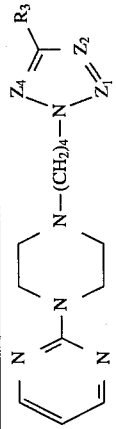

| | | | | | | |
|---|---|---|---|---|---|---|
| 11 | CCl | N | | Oil | 2942, 1586, 1547, 1500, 1447, 1359, 1259, 1245, 983 (film) | CDCl₃ | 1.45–1.84(c.a., 4H); 2.26–2.57(c.a., 9H); 3.74–4.05(c.a., 6H) 6.48(t, J=4.7Hz, 1H); 8.30(d, J=4.7Hz, 2H) |
| 12 | CMe | N | | Oil | 2938, 1585, 1547, 1495, 1446, 1360, 1260, 983, 638 (film) | CDCl₃ | 1.34(t, J=7.1, 3H); 1.66(m, 4H); 2.31–2.72 (c.a., 8H); 3.77–3.92(c.a., 6H); 6.47(t, J=4.7 Hz, 1H) 6.87(d, J=10Hz, 2H); 8.26(d, J=4.7Hz, 2H) |
| 13 | CEt | N | | Oil | 2941, 1585, 1547, 1500, 1446, 1360, 1260, 983, 774 (film) | CDCl₃ | 1.45(m, 2H); 1.73(m, 2H); 2.19–2.42(c.a., 6H); 3.77(t, J=5.1Hz, 4H); 4.01(t, J=7.3Hz, 2H); 6.47(t, J=4.7Hz, 1H); 6.94–7.61(c.a., 7H); 8.27(d, J=4.7Hz, 2H) |
| 14 | CPh | N | O=COMe | 92–94° C. | 2800, 1713, 1585, 1544, 1483, 1360, 1223, 1117, 985 (KBr) | CDCl₃ | 1.45(m, 2H); 1.72(m, 2H); 2.29–2.39(c.a., 6H); 3.65–3.74(c.a., 7H); 4.01(t, J=6.8Hz, 2H) 6.47 (t, J=4.7Hz, 1H); 7.67(s, 1H); 7.81(s, 1H); 8.24(d, J=4.7Hz, 2H) |
| 15 | CH | N | Ph | 105–107° C. | 2944, 1585, 1548, 1500, 1447, 1360, 1260, 983 (KBr) | d₆-DMSO | 1.45(m, 2H); 1.73(m, 2H); 2.21–2.45(c.a., 6H); 3.60–3.75(c.a., 4H); 4.03(t, J=6.8Hz, 2H) 6.47 (t, J=4.7Hz, 1H); 7.21–7.79(c.a., 7H); 8.25(d, J=4.7Hz, 2H) |
| 16 | CH | N | C—CH=CH—CH=CH— | | 2944, 1581, 1542, 1488, 1466, 1355, 1259, 741 (KBr) | d₆-DMSO | 1.40(m, 2H); 1.82(m, 2H); 2.26–2.42(c.a., 6H); 3.62–3.71(c.a., 4H); 4.24(t.J=6.9Hz, 2H) 6.56(t, J=4.7Hz, 1H); 7.16–7.26 c.a., 2H); 7.55–7.70(c.a., 2H); 8.22–8.34(c.a., 3H) |
| 17 | CH | N | C—N=CH—CH=CH— | | 2935, 1578, 1545, 1482, 1443, 1409, 1357, 1256, 982, 751 (KBr) | d₆-DMSO | 1.45(m, 2H); 1.90(m, 2H); 2.23–2.50(c.a., 6H); 3.6(t, J=4.8Hz, 4H); 4.3(t, J=7.0Hz, 2H); 6.5(t, J=4.7Hz, 1H); 7.25(dd, J=4.7Hz, 1H); 8.05(d, J=7.9Hz, 1H); 8.30–8.48(c.a., 4H) |
| 18 | CH | N | C—CH=CH—CH=N— | 104° C. | 2944, 2828, 1609, 1582, 1543, 1487, 1460, 1355, 1260, 982, 800 (KBr) | d₆-DMSO | 1.42(m, 2H); 1.84(m, 2H); 2.28–2.49(c.a., 6H); 3.60–3.69(c.a., 4H); 4.03(t, J=7.0Hz, 2H) 6.5(t, J=4.7Hz, 1H); 7.28 (dd, J=4.7Hz, 1H); 8.07(d, J=7.9Hz, 1H); 8.29–8.50(c.a., 4H) |
| 19 | N | N | C—CH=CH—CH=CH— | 134° C. | 2940, 2818, 1590, 1544, 1498, 1360, 1259, 984, 749 (KBr) | d₆-DMSO | 1.43(m, 2H); 1.97(m, 2H); 2.24–2.53(c.a., 6H); 3.66(t, J=5.1Hz, 4H); 4.75(t, J=6.8Hz, 2H); 6.60(t, J=4.7Hz, 1H); 7.52(m, 2H); 8.01 (m, 2H); 8.31(s, 1H); 8.36(s, 1H) |
| 20 | CCl | N | C—CH=CH—CH=CH— | 89–90.5° C. 153–145° C. | 2940, 1583, 1542, 1491, 1466, 1443, 1383, 1264, 1128, 981, 742 (KBr) | d₆-DMSO | 1.50(m, 2H); 1.81(m, 2H); 2.20–2.42(c.a., 6H); 3.67(m, 4H); 4.28(t, J=7Hz, 2H); 6.58(t, J=4.7Hz, 1H); 7.30(m, 1H); 7.60(m, 2H); 8.31(d, J=4.7Hz, 2H) |

TABLE I-continued

| Example | $Z_1$ | $Z_2$ | $R_3$ | M.p. | IR cm$^{-1}$ | NMR Solvent | $^1$H NMR(100 MHz), δ, J=Hz |
|---|---|---|---|---|---|---|---|
| 21 | CH | N | H | 69–71° C. | 2942, 1582, 1546, 1458, 1448, 1360, 1261, 1138, 1011, 983, 680 (KBr) | CDCl$_3$ | 1.55(m, 2H); 1.96(m, 2H); 2.32–2.51(c.a. 6H); 3.81(t, J=5.1Hz, 4H); 4.21(t, J=7.0Hz, 2H); 6.47(t, J=4.7Hz, 1H); 7.95(s, 1H); 8.09 (s, 1H); 8.29 (d, J=4.7Hz, 2H) |
| 22 | N | N | —CH=CH—CH=CH— | 97.4–98.2° C. | 2946, 2863, 2823, 1585, 1547, 1483, 1358, 1256, 982, 799, 761 (KBr) | d$_6$-DMSO | 1.34–1.56(m, 2H); 1.97–2.13(m, 2H); 2.18–2.48 (c.a. 6H); 3.65(t, J=5.3Hz, 4H); 4.75(t, J=6.8Hz, 2H); 6.56(t, J=4.7Hz, 1H); 7.40(dd, J=6.5Hz, J=3.1Hz, 2H); 7.90(dd, J=6.6Hz, J=3.3Hz, 2H); 8.28(s, 1H); 8.33(s, 1H) |
| 23 | CMe | C—CH=CH—CH=CH— | H | 101–102° C. | 2938, 2820, 1583, 1542, 1494, 1405, 1357, 1258, 983, 798, 744 (KBr) | CDCl$_3$ | 1.56–1.93(c.a. 4H); 2.30–2.47(c.a. 6H); 2.58(s, 3H); 3.79(t, J=5.2Hz, 4H); 4.10(t, J=7.3Hz, 2H); 6.43(t, J=4.7Hz, 1H); 7.22(m, 3H); 7.67 (m, 1H); 8.26(d, J=4.7Hz, 2H) |
| 24 | CH | $\begin{array}{c}CH_3 \quad CH_3 \\ | \quad | \\ C—CH=C\text{—}\text{—}C=CH\text{—}\end{array}$ | | 105–106° C. | 2946, 1584, 1542, 1491, 1466, 1362, 1262, 983, 800, 742 (KBr) | CDCl$_3$ | 1.50(m, 2H); 1.85(m, 2H); 2.25–2.43(c.a. 12H); 3.76(t, J=5.0Hz, 4H); 4.07(t, J=7.0Hz, 2H); 6.40(t, J=4.7Hz, 1H); 7.11(s, 1H); 7.51 (s, 1H); 7.71(s, 1H); 8.23(d, J=4.7Hz, 2H) |

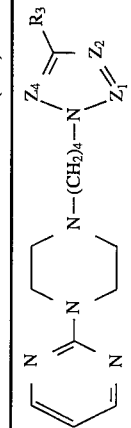

| Example | $Z_1$ | $Z_2$ | $Z_4$ | $R_3$ | M.p. | IR cm$^{-1}$ | NMR Solvent | $^1$H NMR(100 MHz), δ, J=Hz |
|---|---|---|---|---|---|---|---|---|
| 25 | N | CH | CH | H | Oil | 2942, 2815, 1586, 1547, 983 (film) | CDCl$_3$ | 1.50(m, 2H); 1.9(m, 2H); 2.40(m, 6H); 3.80(m, 4H); 4.12(t, 2H, J=6.9); 6.20(t, 1H, J=1.6); 6.40(t, 1H, J=4.7); 7.42(dd, 2H, J=1.6); 8.25(d, 2H, J=4.7) |
| 26 | N | CMe | CMe | H | Oil | 1590, 1550, 1350, 1260, 980 (film) | CDCl$_3$ | 1.58(m, 2H); 1.85(m, 2H); 2.20(s, 3H); 2.25(s, 3H); 2.44(m, 6H); 3.81(m, 4H); 3.97(t, 2H, J=7.2); 5.78(s, 1H); 6.43(t, 1H, J=4.7); 8.27(d, 2H, J=4.7) |
| 27 | N | CMe | CMe | NO$_2$ | Oil | 1590, 1550, 1350, 1260, 980 (film) | CDCl$_3$ | 1.60(m, 2H); 1.90(m, 2H); 2.49(m, 9H); 2.63(s, 3H); 3.82(m, 4H); 4.09(t, 2H, J=7); 6.48(t, 1H, J=4.7); 8.29(d, 2H, J=4.7) |
| 28 | N | CH | CH | Me | Oil | 1590, 1550, 1500, 1360, 1260, 980 (film) | CDCl$_3$ | 1.52(m, 2H); 1.95(m, 2H); 2.05(s, 3H); 2.37(m, 6H); 3.81(m, 4H); 4.05(t, 2H, J=6.8); 6.41(t, 1H, J=4.7); 7.13(s, 1H); 7.27(s, 1H); 8.23(d, 2H, J=4.7) |
| 29 | N | CH | CH | —CH=CH—CH=CH— | Oil | 2930, 1590, 1500, 1360, 1310 | CDCl$_3$ | 1.51(m, 2H); 1.98(m, 2H); 2.36(m, 6H); 3.77(m, 4H); 4.39(t, 2H, J=6.9); 6.40(t, 1H, J=4.7); 7.0–7.7 (m, 4H); 7.95(s, 1H); 8.25(d, 2H, J=4.7) |
| 30 | N | CMe | CMe | Br | Oil | 2930, 1590, 1550, 1500, 1360, 1310 | CDCl$_3$ | 1.55(m, 2H); 1.81(m, 2H); 2.18(s, 3H); 2.20(s, 3H); 2.38(m, 4H); 3.80(m, 4H); 3.99(t, 2H, |

TABLE I-continued

| | | | | | | |
|---|---|---|---|---|---|---|
| 31 | N | CH | NO₂ | 94–96° C. | 1260, 980 (film) 1584, 1524, 1480, 1444, 1406, 1359, 1305, 819 (KBr) | CDCl₃ | J=6.9); 6.42(t, 1H, J=4.7); 8.25(d, 2H, J=4.7) 1.5(m, 2H); 1.93(m, 2H); 2.38(m, 6H); 3.76(m, 4H); 4.15(t, 2H, J=6.7); 6.42(t, 1H, J=4.7); 8.01(s, 1H); 8.12(s, 1H); 8.24(d, 2H, J=4.7) |
| 32 | N | CH | Cl | 2 HCl 195–8° C. | 3429, 2688 1636, 1620 1346, 1218 971 | d₆-DMSO | 1.69(m, 2H); 1.81(m, 2H); 2.98(m, 2H); 3.08 (m, 2H); 3.39–3.53(m, 4H); 4.12(t, 2H); 4.67(d, 2H); 6.77(t, 1H); 7.53(d, 1H); 8.04(d, 1H); 8.45(d, 2H) |
| 33 | N | CH | EtOOC— | oil | 1715, 1586, 1222, 983 (film) | CDCl₃ | 1.34(t, 3H, J=7.1); 1.54(m, 2H); 1.90(m, 2H); 2.46(m, 6H); 3.81(m, 4H); 4.25(m, 4H); 6.47(t, 1H, J=4.7); 7.90(s, 2H); 8.29(d, 2H, J=4.7) |
| 34 | N | CMe | H | oil | 1586, 1541, 1360, 983 (film) | CDCl₃ | 1.54(m, 2H); 1.85(m, 2H); 2.28(s, 3H); 2.45(m, 6H); 3,81(m, 4H); 4.07(t, 2H, J=7); 6.28(s, 1H); 6.43(t, 1H, J=4.7); 7.33(m, 4H); 7.75(m, 2H); 8.26(d, 2H, J=4.7) |
| 35 | N | CH | Br | oil | 1586, 1547, 1360, 984 (film) | CDCl₃ | 1.52(m, 2H); 1.89(m, 2H); 2.44(m, 6H); 3.62 (m, 4H); 4.11(t, 2H, J=6.7); 6.46(t, 1H, j=4.6); 7.42(s, 1H); 7.45(s, 1H); 8.29(d, 2H, J=4.6) |
| 36 | N | CH | C≡N | 94–95° C. | 3076, 2231, 1587, 1551, 1258, 982 | (KBr) CDCl₃ | 1.54(m, 2H); 1.96(m, 2H); 2.40(m, 6H); 3.81 (m, 4H); 4.20(t, 2H, J=6.9); 6.48(t, 1H, J= 4.7); 7.80(s, 1H); 7.83(s, 1H); 8.29(d, 2H, J=4.7) |
| 37 | N | CH | F | oil | 2944, 1584, 1546, 1507, 1359, 1260, 983 (film) | CDCl₃ | 1.45(m, 2H); 1.96(m, 2H); 2.36(m, 6H); 3.77 (m, 4H); 4.0(t, 2H, J=6.9); 6.47(t, 1H, J= 4.7); 7.27(m, 2H, J=4.8); 8.29(d, 2H, J=4.8) |
| 38 | N | N | H₂N— | Oil | 1586, 1548, 1360, 984 (film) | CDCl₃ | 1.50(m, 2H); 1.85(m, 2H); 2.43(broad 2H); 3.8(m, 6H); 4.0(t, 2H, J=6,4); 6.46(t, 1H, J=4.7); 7.10(s, 1H); 8.27(d, 2H, J=4.7) |
| 39 | N | CH | Me—SO₂—NH— | 132° C. | 1582, 1482, 1360, 1150, 983 (KBr) | CDCl₃ | 1.58(m, 2H); 1.93(m, 2H); 2.45(m, 6H); 2.94(m, 3H); 3.8(m, 4H); 4.11(t, 2H, J=6.9); 6.45(t, 1H, J=4.7) 7.4(s, 1H); 7.5(s, 1H); 8.28(d, 2H, J=4.7) |
| 40 | N | CH | Ph—CO—NH— | 134–136° C. | 1646, 1586, 1542, 1349, (KBr) | CDCl₃ | 1.55(m, 2H); 1.79(s, 3H); 1.88(m, 2H); 2.42(m, 6H); 3.80(m, 4H); 4.13(t, 2H, J=6.8); 6.51(t, 1H, J=4.7) 7.49(m, 4H); 7.83(m, 2H); 8.0(s, 1H); 8.11(s, 1H); 8.28(d, 2H, J=4.7) |
| 41 | N | CH | Me—CO—NH— | 80–82° C. | 1650, 1586, 1454, 1364, 1261, 983 (KBr) | CDCl₃ | 1.50(m, 2H); 1.88(m, 2H); 2.11(s, 3H); 2.43(m, 6H); 3.79(m, 4H); 4.8(t, 2H, J=6.8); 6.47(t, 1H, J=4.7) 7.36(s, 1H); 7.93(s, 1H); 8.28(d, 2H, J=4.6); 9.25(s, 1H) |
| 42 | N | CH | Me—CH(Et)—NH— | Oil | 2960, 1585, 1547, 1359, 1260 (film) | CDCl₃ | 1.00(t, 3H, J=7.0); 1.19(d, 3H, J=6.3); 1.6(m, 4H); 1.90(m, 2H); 2.50(m, 6H); 3.0(m, 3H); 3.9(m, 4H); 4.1(t, 2H, J=6.8); 6.52(t, 1H, J=4.7); 6.99(s, 1H) 7.17(s, 1H); 3.37(d, 2H, J=4.7) |
| 43 | N | CCl | F | Oil | 2944, 1585, 1547, 1507, 1359, 1260, 984 (film) | CDCl₃ | 1.52(m, 2H); 1.90(m, 2H); 2.40(m, 6H); 3.80(m, 4H); 4.0(t, 2H, J=4.8); 6.45(t, 1H, J=4.7); 7.30(d, 1H, J=4.8); 8.29 (d, 1H, J=4.8) |

TABLE I-continued

| | | | | | |
|---|---|---|---|---|---|
| 44 | N | CH | Me-O-⟨C6H4⟩- | 79–82° C. | 2390, 1589, 1545, 1495, 1360, 1247, 983, 835, 799 (KBr) | CDCl₃ | 1.62(m, 2H); 1.88(m, 2H); 2.45(m, 6H); 3.81 (m, 7H); 4.16(t, 2H, J=6.8); 6.46(t, 1H, J=4.7); 6.9d(2H, J=4.4); 7.4d(2H, J=4.4); 7.55(d, 1H); 87.7(s, 1H) 8.28(d, 2H, J=2.4) |
| 45 | N | CH | Ph-⟨C6H4⟩- | 108–110° C. | 2946, 1586, 1549, 1485, 1395, 1257, 982, 951, 830 (KBr) | CDCl₃ | 1.6(m, 2H); 1.9(m, 2H); 2.46(m, 6H); 3.8(m, 4H); 4.16(t, 2H, J=6.8); 6.4(t, 1H, J=4.7); 7.36(d, 4H, J=1.3); 7.7(d, 2H, J=6.2); 8.28 (d, 2H, J=2.3) |
| 46 | N | CH | ⟨pyrrole-N⟩ | Oil | 2943, 1586, 1487, 1359, 1260, 984, 726 (film) | CDCl₃ | 1.55(m, 2H); 1.80(m, 2H); 2.45(m, 6H); 3.81(t, 4H, J=5); 4.12(t, 2H, J=7); 6.25(2H, t, J=2); 6.44(1H, t, J=4.7); 6.84(m, 2H); 7.5(d, 2H, J=5); 8.27(d, 2H, J=4.7) |
| 47 | N | CH | ⟨Ph⟩ | 39–42° C. | 2942, 1585, 1493, 1446, 1359, 1258, 983, 760 (film) | CDCl₃ | 1.6(m, 2H); 1.9(m, 2H); 2.5(m, 4H); 3.8(m, 6H); 4.2(t, 2H, J=6.8); 6.7(t, 1H, J=4.7); 7.2–7.7(compl. abs., 5H); 8.0(s, 1H); 8.2(s, 1H); 8.4(d, 2H, J=2.3) |
| 48 | N | CPh | H | 80–82° C. | 2942, 1585, 1547, 1485, 1359, 1260, 983, 763, 697 (film) | CDCl₃ | 1.6(m, 2H); 1.9(m, 2H); 2.35(m, 6H); 3.8(m, 4H); 4.2(t, 2H, J=6.8); 6.4(t, 1H, J=4.7); 6.6 (s, 1H); 7.2–7.4(compl. abs., 8H); 7.8(m, 2H); 8.25(d, 2H, J=2.4) |
| 49 | N | CH | ⟨C6H5-CO₂-NH-⟩ | 92–95° C. | 2931, 1584, 1548, 1490, 1358, 1167, 983 (KBr) | CDCl₃ | 1.45(m, 2H); 1.85(m, 2H); 2.40(m, 6H); 3.80 (m, 4H); 4.0(t, 2H, J=6.7); 6.47(t, 1H, J=4.6); 7.0(s, 1H); 7.5(m, 6H); 8.3(d, 2H, J=4.6) |
| 50 | N | CH | ⟨Me-C6H4-CO₂-NH-⟩ | 108–110° C. | 2943, 1585, 1548, 1446, 1360, 1161, 984 (KBr) | CDCl₃ | 1.5(m, 2H); 1.85(m, 2H); 2.28(m, 9H); 3.8(m, 4H); 4.0(m, 2H); 6.45(t, 1H, J=4.7); 7–7.65 (m, 6H); 8.27(d, 2H, J=4.7) |
| 51 | N | CH | n-Bu-SO₂-NH- | Oil | 2941, 15489, 1448, 1360, 1146, 964, 755 (film) | CDCl₃ | 0.91(t, 3H, J=6.8); 1.45(m, 4H); 1.85(m, 4H); 2.40(m, 6H); 3.0(m, 2H); 3.80(m, 4H); 4.11(t, 2H, J=6.5) 6.5(t, 1H, J=4.7); 7.4(m, 2H); 7.5(s, 1H); 8.3(d, 2H, J=4.7) |
| 52 | N | CH | n-Pr-SO₂-NH- | Oil | 2940, 1586, 1548, 1447, 1360, 1146, 984, 755 (film) | CDCl₃ | 1.0(t, 3H, J=7.1); 1.55(m, 2H); 1.9(m, 4H); 2.45(m, 6H); 3.0(t, 2H, J=7.4); 3.8(m, 4H); 4.1(t, 2H, J=6.4); 6.46(t, 1H, J=4.7) 7.35 (m, 2H, 5H); 7.5(m, 1H); 8.3(d, 2H, J=4.7) |
| 53 | N | CH | Et-SO₂-NH- | Oil | 2943, 1586, 1548, 1447, 1360, 1146, 984, 754 (film) | CDCl₃ | 1.36(m, 5H); 1.9(m, 2H); 2.45(m, 6H); 3.0(m, 2H); 3.6(m, 4H); 4.1(t, 2H, J=6.4); 6.45(t, 1H, J=4.7) 7.39(s, 1H); 7.51(s, 1H); 8.3(d, 2H, J=4.7) |
| 54 | N | CMe | -SO₂-N-Me₂ | Oil | 2939, 1547, 1448, 1360, 1290, 983, 951, 788 | CDCl₃ | 1.7(m, 2H); 2.3–3.0(compl. abs., 18H); 3.8(m, 4H); 4.0(t, 2H, J=6.8); 6.45(m, 2H); 6.5(t, 1H, J=4.7); 8.2 (d, 2H, J=2.35) |

TABLE I-continued

| Example | $Z_1$ | $Z_2$ | $R_3$ | $Z_4$ | | | | M.p. | IR cm$^{-1}$ | NMR Solvent | $^1$H NMR |
|---|---|---|---|---|---|---|---|---|---|---|---|
| 55 | N | CH | CH | CH | | $-SO_2-N-Me_2$ | | 100–102° C. | 3135, 2943, 1586, 1512, 1357, 1328, 1156, 982, 728 (KBr) | CDCl$_3$ | 1.6(m, 2H); 1.9(m, 2H); 2.3–2.7(compl. abs., 13H) 3.8(m, 4H); 4.2(t, 2H, J=6.8); 6.4(t, 1H, J=4.7); 7.75(d, 1H, J=4.4); 8.28(d, 2H, J=2.4) (film) |
| 56 | N | CH | CH | CH | | $-SO_3-H$ | | 230–235° C. | 3330, 1590, 1556, 1449, 1220, 1178, 1178, 1049, 971, 656 (KBr) | D$_2$O | 1.95(m, 2H); 3.3(m, 6H); 4.0(s, 5H); 4.27(t, 2H, J=6.1); 6.8(t, 1H, J=4.8); 7.8(s, 1H); 8.0(s, 1H); 8.43(d, 2H, J=2.4) |
| 57 | CH | N | Cl | CH | | H | | Oil | 2940, 1585, 1500, 1360, 1260, 975, (film) | CDCl$_3$ | 1.6(m, 2H); 1.8(m, 2H); 2.5(m, 6H); 3.80(m, 6H); 6.5(t, 1H, J=4.7); 6.9(s, 1H); 7.1(s, 1H); 7.5(s, 1H); 8.4(d, 2H, J=4.7) |
| 58 | CMe | N | Cl | CH | | H | | Oil | 2941, 1586, 1547, 1499, 1359, 1259, 983 (film) | CDCl$_3$ | 1.72(m, 4H); 2.37(s, 3H); 2.44(m, 6H); 3.80(m, 6H); 6.45(t, 1H, J=4.7); 6.85(d, 2H, J=4.5); 8.27(d, 2H, J=4.7) |
| 59 | CH | N | Cl | CCl | | Cl | | 69–71° C. | 2946, 1584, 1543, 1492, 1359, 1254, 983, 797 (KBr) | CDCl$_3$ | 1.4–2.1(compl. abs., 4H); 2.46(m, 6H); 3.86(m, 6H); 6.47(t, 1H, J=4.7); 7.38(s, 1H); 8.29(d, 2H, J=4.7) |

| Example | $Z_1$ | $Z_2$ | $R_3$ | $Z_4$ | $R_7$ | $R_8$ | $R_9$ | M.p. | IR cm$^{-1}$ | NMR Solvent | $^1$H NMR(100 MHz), δ, J=Hz |
|---|---|---|---|---|---|---|---|---|---|---|---|
| 60 | N | CH | Cl | CH | H | H | MeO— | 76–77° C. | 2833, 2815, 1511, 1448, 1247, 1029, 979, 824 (KBr) | d$_6$-DMSO | 1.43(m, 2H); 1.78(m, 2H); 1.71–2.48(c.a., 6H); 2.93–3.02(m, 4H); 3.67(s, 3H); 4.09(t, J=6.8 Hz, 2H); 6.83(s, 4H); 7.52(s, 1H); 7.98(s, 1H) |
| 61 | CMe | N | Cl | CCl | H | H | MeO— | 73–75° C. | 2940, 2818, 1512, 1457, 1245, 1183, 1036, 826 (KBr) | d$_6$-DMSO | 1.33–1.87(c.a., 4H); 2.32(s, 3H); 2.41–2.51(c.a., 6H); 2.82–3.0(m, 4H); 3.67(s, 3H); 3.93(t, J=7.2Hz, 2H); 6.83(s, 4H) |
| 62 | N | CH | Cl | CH | MeO— | H | H | Oil | 2941, 2816, 1500, 1450, 1241, 749, (film) | d$_6$-DMSO | 1.39(m, 2H); 1.77(m, 2H); 2.22–2.45(c.a., 6H); 2.92(m, 4H); 3.76(s, 3H); 4.07(t, J=6.0Hz, 2H); 6.87(m, 4H); 7.51(s, 1H); 7.95(s, 1H) |
| 63 | CMe | N | Cl | CCl | MeO— | H | H | 82–83° C. | 2943, 2820, 1502, 1405, 1241, 1030, 746 (KBr) | d$_6$-DMSO | 1.43–1.60(c.a., 4H); 2.33(s, 3H); 2.40–2.50(c.a., 6H); 2.95(m, 4H); 3.76(s, 3H); 3.93(t, J=7.0Hz, 2H); 6.89(m, 4H) |
| 64 | N | CH | Cl | CH | H | MeO— | H | Oil | 2943, 2820, 1601, 1578, 1496, 1451, 1203, 1171, 970 (film) | CDCl$_3$ | 1.52(m, 2H); 1.85(m, 2H); 2.28–2.56(c.a., 6H); 3.16(m, 4H); 3.7(s, 3H); 4.05(t, J=7.0Hz, 2H); 6.4(m, 3H); 7.15(m, 1H); 7.34(s, 1H); 7.40(s, 1H) |
| 65 | CH | CH | H | CH | H | H | MeO— | Oil | 2943, 2815, 1512, 1455, 1244, 1037, 823, 724 (film) | CDCl$_3$ | 1.50–1.80(c.a., 4H); 2.31–2.61(c.a., 6H); 3.06(m, 4H); 3.74(s, 3H); 3.81(t, J=7.0Hz, 2H); 6.1 (m, 2H); 6.6(m, 2H); 6.84(s, 4H) |
| 66 | CH | CH | H | CH | MeO— | H | H | Oil | 2940, 2814, 1500, 1451, 1281, 1241, 1028, 743, 723 | CDCl$_3$ | 1.50–1.85(c.a., 4H); 2.33–2.66(c.a., 6H); 3.10(m, 4H); 3.84–3.96(c.a., 5H); 6.12(t, J=2Hz, 2H); 6.65(t, J=Hz, 2H); 6.93(m, 4H) |

TABLE I-continued

| No. | | | | | | | mp | IR | Solvent | NMR |
|---|---|---|---|---|---|---|---|---|---|---|
| 67 | CH | CH | H | H | H | H | Oil | 2943, 2817, 1600, 1501, 1235, 759, 723, 692 (film) | CDCl$_3$ | 1.41–1.89(c.a., 4H); 2.37(t, J=7,3Hz, 2H); 2.50–2.60(c.a., 4H); 3.18(m, 4H); 3.89(t, J= 6.9Hz, 2H); 6.13(t, J=2.0Hz, 2H); 6.64(t, J=2.0Hz, 2H); 6.83–7.33(c.a., 5H) |
| 68 | CH | CH | Cl | H | H | H | 58–61° C. | 2942, 2819, 1600, 1500, 1450, 1381, 1311, 1240, 1140, 966, 756 (KBr) | CDCl$_3$ | 1.47(m, 2H); 1.84(m, 2H); 2.35(t, J=7.2Hz, 2H); 2.52(m, 4H); 3.16(m, 4H); 4.04(t, J=6.8 Hz, 2H); 6.75–6.94(c.a., 3H); 7.16(s, 1H); 7.23 (s, 1H); 7.35(d, J=7.4Hz, 2H) |
| 69 | CMe | N | Cl | CCl | H | H | Oil | 2944, 2819, 1600, 1532, 1503, 1453, 1404, 1244, 1143, 759, 692 (film) | CDCl$_3$ | 1.43–1.87(c.a., 4H); 2.33(s, 3H); 2.38–2.60(c.a., 6H); 3.17(m, 4H); 3.83(t, J=7Hz, 2H); 6.9 (c.a., 3H); 7.24(m, 2H) |
| 70 | N | CH | Cl | CH | H | H | Oil | 2943, 2817, 1587, 1480, 1443, 1231, 1040, 971, 751, 612 (film) | d$_6$-DMSO | 1.40(m, 2H); 1.78(m, 2H); 2.2–2.6(c.a., 6H); 2.95(m, 4H); 4.08(t, J=6.5Hz, 2H); 6.95–7.41 (c.a., 4H); 7.50(s, 1H); 7.97(s, 1H) |
| 71 | CMe | N | Cl | CCl | H | H | 89–91° C. | 2936, 2818, 1587, 1531, 1480, 1359, 1243, 1229, 1036, 1016, (KBr) | CDCl$_3$ | 1.3–1.8(c.a., 4H); 2.32(s, 3H); 2.35–2.70(c.a., 6H); 2.96(m, 4H); 3.94(t, J=7.2Hz, 2H); 6.90–7.50(c.a., 4H) |
| 72 | N | CH | Cl | CH | Cl | H | Oil | 2944, 2820, 1594, 1564, 1487, 1451, 1433, 1384, 1239, 987, 980 (film) | CDCl$_3$ | 1.3–1.70(m, 2H); 1.70–2.10(m, 2H); 2.39(t, J= 7.4Hz, 2H); 2.59(m, 4H); 3.17(m, 4H); 4.09(t, J=4Hz, 2H); 6.6–6.9(c.a., 3H); 7.15(t, J= 8.0Hz, 1H); 7.37(s, 1H); 7.46(s, 1H) |
| 73 | CMe | N | Cl | CCl | CN | H | 80° (Dec) | 2956, 2848, 2219, 1593, 1488, 1240, 1232, 1010, 765 (KBr) | CDCl$_3$ | 1.45–1.80(c.a., 4H); 2.37(s, 3H); 2.20–2.70(c.a., 6H); 3.23(m, 4H); 3.88(t, J=7.1Hz, 2H); 6.90–7.06(c.a., 2H); 7.30–7.60(c.a., 2H) |
| 74 | CMe | N | Cl | CCl | F | H | Oil | 2944, 2822, 1501, 1406, 1241, 1141, 754 (film) | CDCl$_3$ | 1.30–1.80(c.a., 4H); 2.35(s, 3H); 2.20–2.70(c.a., 6H); 3.10(m, 4H); 3.87(t, J=7Hz, 2H); 6.70–7.07(c.a., 4H) |
| 75 | N | CH | Cl | CH | CN | H | 59° (dec) | 2948, 2823, 2219, 1596, 1488, 1447, 1376, 1231, 971, 762 (film) | CDCl$_3$ | 1.50(m, 2H); 1.86(m, 2H); 2.43(t, J=7Hz, 2H); 2.63(m, 4H); 3.23(m, 4H); 4.11(t, J=6.8 Hz, 2H); 6.80–7.10(c.a., 2H); 7.25–7.65(c.a., 4H) |
| 76 | CMe | N | Cl | CCl | H | CF$_3$ | Oil | 2946, 2821, 1609, 1450, 1357, 1319, 1245, 1163, 1122, 697, (film) | CDCl$_3$ | 1.35–1.75(c.a., 4H); 2.35(s, 3H); 2.30–2.65(c.a., 6H); 3.22(m, 4H); 3.87(t, J=7.1Hz, 2H); 6.95–7.10(c.a., 2H); 7.32(m, 1H) |
| 77 | N | CH | Cl | CH | H | CF$_3$ | Oil | 2947, 2821, 1610, 1450, 1357, 1319, 1163, 1123, 696 (film) | CDCl$_3$ | 1.49(m, 2H); 1.89(m, 2H); 2.38(t, J=7.2Hz, 2H); 2.53(m, 4H); 3.21(m, 4H); 4.08(t, J=6.8 Hz, 2H); 6.95–7.12(c.a., 3H); 7.20–7.45(m, 3H [δ=7.36 s, 1H, δ=7.40 s, 1H] |
| 78 | N | CH | Cl | CH | F | H | Oil | 2944, 2820, 1501, 1451, 1239, 971, 753 (film) | CDCl$_3$ | 1.50(m, 2H); 1.89(m, 2H); 2.41(t, J=7.2Hz, 2H); 2.59(m, 4H); 3.10(m, 4H); 4.09(t, J=6.9 Hz); 6.80–7.10(c.a., 4H); 7.37(s, 1H); 7.40(s, 1H) |

TABLE I-continued $$Ar-N\underset{}{\overset{}{\bigcirc}}N-(CH_2)_4-N\underset{Z_1}{\overset{Z_4}{\underset{}{\bigvee}}}\overset{R_3}{\underset{Z_2}{}}$$

| Example | $Z_1$ | $Z_2$ | $Z_4$ | $R_3$ | Ar | M.p. | IR cm$^{-1}$ | NMR Solvent | $^1$H NMR(100 MHz), δ, J=Hz |
|---|---|---|---|---|---|---|---|---|---|
| 79 | N | CH | CH | Cl | benzisothiazol-3-yl | Oil | 2943, 2815, 1493, 1451, 1423, 1383, 1307, 1261, 970, 739 613 (film) | CDCl$_3$ | 1.50(m, 2H); 1.85(m, 2H); 2.45(t, J=7.2Hz, 2H); 2.60(t, J=4.7Hz, 4H); 3.53(t, J=5.0 Hz, 4H); 4.07(t, J=7.0Hz, 2H); 7.35(m, 4H); 7.85(m, 2H) |
| 80 | CMe | N | CCl | Cl | benzisothiazol-3-yl | Oil | 2944, 2816, 1533, 1493, 1422, 1380, 1280, 1246, 1139, 1017, 754, 665 (film) | CDCl$_3$ | 1.55–1.85(c.a., 4H); 2.34–2.49(c.a., 5H); 2.62(t, J=4.7Hz, 4H); 3.53(t, J=5.0Hz, 4H); 3.84 (t, J=7.0Hz, 2H); 7.37(m, 2H); 7.83(m, 2H) |
| 81 | CH | N | N | H | benzisothiazol-3-yl | 102–4° C. | 2943, 2809, 1493, 1426, 1275, 1152, 1007, 738, 678 | CDCl$_3$ | 1.55(m, 2H); 1.97(m, 2H); 2.45(t, J=7.3, 2H); 2.64(c.a., 4H); 3.55(c.a., 4H); 4.22(t, J=6.9 Hz, 2H); 7.35(m, 1H); 7.46(m, 1H); 7.80(d, J= 8Hz, 1H); 7.90(d, J=8Hz, 1H); 7.95(s, 1H); 8.08(s, 1H) |
| 82 | CH | N | C—CH=CH—CH=CH | | benzisothiazol-3-yl | Oil | 2944, 2828, 1495, 1459, 1422, 1285, 746 (film) | CDCl$_3$ | 1.56(m, 2H); 1.96(m, 2H); 2.42(t, J=7.1Hz, 2H); 2.61(c.a. 4H); 3.53(c.a., 4H); 4,19(t, J= 7.0Hz, 2H); 7.10–7.50(c.a., 5H); 7.70–7.90(c.a., 4H) |
| 83 | N | CH | CH | Br | pyrimidin-4-yl | 84.6° C. | 2952, 1583, 1526, 1365, 1311, 950, (KBr) | CDCl$_3$ | 1.57(m, 2H); 1.90(m, 2H); 2.45(m, 6H); 3.80(t, 4H, J=6.8); 7.44(d, 2H, J=4); 8.29(s, 2H) |

TABLE I-continued

| 84 | N | CH | CH | Cl | [Ar-pyrimidine structure] | 85–86° C. | 1585, 1525, 1495, 1364, (KBr) | CDCl₃ | 1.50(m, 2H); 1.86(m, 2H); 2.40(m, 6H); 3.76(m, 4H); 4.08((m, 2H); 7.4(t, 2H, J=6.9); 8.25 (s, 2H) |

Inhibitory activity on gastric acid secretion, Shay Method [Shay, H., Komarov, S. A., Fels, S. S., Merange, D., Grvenstein, M., Siplet, H.: Gastroenterology, 5, 43 (1945)—Visscher, F. E., Seay, P. H., Taxelaar, A. P., Veldhamp, W., Vander Brook, M. J.: J. Pharmac. Exp. Ther., 110, 188 (1954)—"Animal Experiments in Pharmacological Analysis", F. R. Domer; C. C. Thomas Pub, Springfield, Ill., USA, 1970, p. 140].

In this test, male Wistar rats weighing 200 to 250 grams are used, which rats are denied food from the day prior to that of the test, with free access to water. Batches which each contain at least 4 animals are used.

The rats are anesthetized with ethyl ether, a laparotomy is carried out on them and their pylori are ligatured, and then the abdominal incision is stitched up. Administration of the products, with the vehicle for the control batch, is carried out intraduodenally (i.d.) before stitching up the abdominal incision. The dose administered for the first test is 40 mg/kg and the 50% effective dose ($ED_{50}$) by the i.d. route is also determined in a second test. The vehicle used is 5% w/v gum arabic in doubly-distilled water.

Two hours after ligaturing the pylorus, the rats are sacrificed by prolonged anesthesia with ethyl ether and the volume of the gastric juice is measured and the total acidity is determined using a pH meter equipped with an automatic burette. The percentage of inhibition of the gastric acid secretion is determined, with respect to the control batch, for each product and for each dose tested.

The results obtained for some of the derivatives of the present invention are summarized, as non-limiting examples, in Table II.

TABLE II

Inhibition of gastric acid secretion in rats. Shay Method

| Example No. | Percentage of inhibition of gastric acid secretion (Dose = 40 mg/kg, i.d. route) | $ED_{50}$ (mg/kg, i.d. route) |
|---|---|---|
| 1 | 90% | 12 |
| 2 | 44% | 46 |
| 3 | 63% | 30 |
| 6 | 41% | 52 |
| 7 | 40% | 47 |
| 9 | 35% | 45 |
| 10 | 81% | 19 |
| 11 | 81% | 14 |
| 12 | 37% | 52 |
| 13 | 44% | 45 |
| 15 | 53% | 36 |
| 16 | 71% | 25 |
| 17 | 63% | 19 |
| 19 | 49% | 42 |
| 21 | 71% | 4.4 |
| 22 | 55% | 34 |
| 24 | 59% | 36 |
| 25 | 85% | 21 |
| 27 | 63% | 17 |
| 29 | 81% | 21 |
| 31 | 90% | 2.7 |
| 32 | 78% | 15 |
| 34 | 45% | 50 |
| 35 | 64% | 11 |
| 36 | 78% | 2.1 |
| 37 | 79% | 17 |
| 38 | 59% | 32 |
| 39 | 85% | 18 |
| 40 | 61% | 26 |
| 41 | 46% | 40 |
| 42 | 85% | 11 |
| 44 | 81% | 31 |
| 45 | 74% | 12 |
| 46 | 92% | 9.5 |
| 47 | 88% | 11 |
| 52 | 54% | 40 |
| 53 | 90% | 6.4 |
| 59 | 75% | 20 |
| 60 | 63% | 26 |
| 61 | 86% | 13 |
| 62 | 81% | 13 |
| 63 | 89% | 10 |
| 64 | 68% | 20 |
| 66 | 65% | 27 |
| 67 | 90% | 8.7 |
| 68 | 94% | 13 |
| 69 | 71% | 7.6 |
| 70 | 81% | 11 |
| 71 | 73% | 9.1 |
| 72 | 88% | 21 |
| 73 | 90% | 4.2 |
| 74 | 94% | 5.0 |
| 75 | 94% | 8.4 |
| 76 | 96% | 2.1 |
| 77 | 82% | 9.2 |
| 78 | 87% | 10 |
| 79 | 82% | 20 |
| 80 | 88% | 7.1 |
| 81 | 82% | 5.2 |
| 82 | 53% | 15 |
| 83 | 45% | 50 |
| 84 | 41% | 42 |
| Cimetidine | 69% | 11.5 |

In human therapeutics, the administration dose is, of course, a function of the seriousness of the condition to be treated. It will generally be between approximately 5 and approximately 100 mg/day. The derivatives of the invention will, for example, be administered in the form of tablets, solutions or suspensions, or else gelatin capsules. Two specific pharmaceutical dosage forms will be shown below, by way of examples.

Tablet formula example

| | |
|---|---|
| Compound of Example 32 | 5 mg |
| Lactose | 60 mg |
| Microcrystalline cellulose | 25 mg |
| Povidone | 5 mg |
| Pregelatinized starch | 3 mg |
| Colloidal silicon dioxide | 1 mg |
| Magnesium stearate | 1 mg |
| Tablet weight | 100 mg |

Gelatin capsule formula example

| | |
|---|---|
| Compound of Example 32 | 10 mg |
| Polyoxyethylenated glycerol | 135 mg |
| Glyceryl behenate | 5 mg |
| Excipient: soft gelatin q.s. | 150 mg |

Taking into account the advantageous pharmacological properties attached to the compounds of general formula I, the present invention applies to the application of these compounds as medicaments, to the pharmaceutical compositions containing them and to their use for the manufacture of medicaments intended for the treatment of gastrointestinal diseases, in particular for the manufacture of inhibitory agents of gastric acid secretion and of anti-ulcer agents.

We claim:
1. A method of treating gastrointestinal diseases characterized by gastric acid hypersecret that comprises administering a therapeutically effective amount to a patient in need of such treatment of a derivative of general formula I:

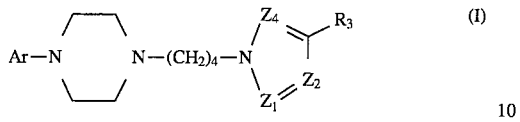

in which Ar represents an optionally nitrogenous aromatic radical chosen from the 2-pyrimidine and 3-(1,2-benzisothiazole), $Z_1$ represents a nitrogen atom or an optionally substituted carbon atom which can be represented by: $C-R_1$, $Z_2$ represents a nitrogen atom or an optionally substituted carbon atom which can be represented $C-R_2$, $Z_4$ represents a nitrogen atom or an optionally substituted by: carbon atom which can be represented by: $C-R_4$, and $R_1$, $R_2$, $R_3$ and $R_4$, which are identical or different and which can also form part of another, optionally aromatic ring, represent a hydrogen atom, a halogen, a lower alkyl radical, a nitro radical, a hydroxyl radical, an alkoxy radical, a cyano radical, a carboxyl radical, a carboxamido radical, an alkyl carboxylate radical, an aryl or substituted aryl radical, a sulfo radical, a sulfonamido radical which is optionally substituted on the amino group, or an amino radical, and its therapeutically acceptable salts.

2. A method as in claim 1 wherein the derivative of general formula I is selected from the group consisting of:

1-{4-[4-(2-pyrimidinyl)-1-piperazinyl]butyl}pyrrole,

1-{4-[4-(2-pyrimidinyl)-1-piperazinyl]butyl}carbazole,

1-{4-[4-(2-pyrimidinyl)-1-piperazinyl]butyl}indole, 2,3-diphenyl-1-{4-[4-(2-pyrimidinyl)-1-piperazinyl}butyl}indole, 4-carboxamido-1-{4-[4-(2-pyrimidinyl)-1-pierazinyl]butyl}-1H-pyrazole, 4-carboxy-1-{4-[4-(2-pyrimidinyl-1-piperazinyl]butyl}-1H-pyrazole, 3-methyl-5-trifluoromethyl-1-{4-[4-(2-pyrimidinyl)-1-piperazinyl]butyl}-1H-pyrazole, 4,5-diphenyl-1-{4-[4-(2-pyrimidinyl)-1-piperazinyl]butyl}-1H-imidacole, 2,4,5-triphenyl-1-{4-[4-(2-pyrimidinyl)-1-piperazinyl]butyl}-1H-imidazole, 4,5-diphenyl-2-methyl-1-{4-[4-(2-pyrimidinyl)-1-piperazinyl]butyl}-1H-imidazole, 4,5-dichloro-2-methyl-1-{4-[4-(2-pyrimidinyl)-1-piperazinyl]butyl}-1H-imidazole, 2-ethyl-1-{4-[4-(2-pyrimidinyl)-1-piperazinyl]butyl}-1H-imidazole, 2-phenyl-1-{4-[4-(2-pyrimidinyl)-1-piperazinyl]butyl}-1H-imidazole, 4-methoxycarbonyl-1-{4-[4-(2-pyrimidinyl)-1-piperazinyl]butyl}-1H-imidazole, 4-phenyl-1-{4-[4-(2-pyrimidinyl)-1-piperazinyl]butyl}-1H-imidazole, 1-{4-[4-(2-pyrimidinyl)-1-piperaziny]butyl}-1H-benzimidazole, 1-{4-[4-(2-pyrimidinyl)-1-piperazinyl]butyl}-1H-imidazo[5,4-b]pyridine, 1-{4-[4-(2-pyrimidinyl)-1-piperazinyl]butyl}-1H-imidazo[4,5-b]pyridine, 1-{4-[4-(2-pyrimidinyl)-1-piperazinyl]butyl}-1H-benzotriazole, 2-chloro-1-{4-[4-(2-pyrimidinyl)-1-piperazinyl]butyl}-1H-benzimidazole, 1-{4-[4-(2-pyrimidinyl)-1-piperazinyl]butyl}-1H-1,2,4-triazole, 2-{4-[4-(2-pyrimidinyl)-1-piperazinyl]butyl}-2H-benzotriazole, 2-methyl-1-{4-[4-(2-pyrimidinyl)-1-piperazinyl]butyl}-1H-benzimidazole, 5,6-dimethyl-1-{4-[4-(2-pyrimidinyl)-1-piperazinyl]butyl}-1H-benzimidazole, 1-{4-[4-(2-pyrimidinyl)-1-piperazinyl]butyl}-1H-pyrazole, 3,5-dimethyl-1-{4-[4-(2-pyrimidinyl)-1-piperazinyl]butyl}-1H-pyrazole, 3,5-dimethyl-4-nitro-1-{4-[4-(2-pyrimidinyl)-1-piperazinyl]butyl}-1H-pyrazole, 4-methyl-1-{4-[4-(2-pyrimidinyl)-1-piperazinyl]butyl}-1H-pyrazole, 1-{4-[4-(2-pyrimidinyl)-1-piperazinyl]butyl}-1H-indazole, 4-bromo-3,5-dimethyl-1-{4-[4-(2-pyrimidinyl)-1-piperazinyl]butyl}-1H-pyrazole, 4-nitro-1-{4-[4-(2-pyrimidinyl)-1-piperazinyl]butyl}-1H-pyrazole, 4-chloro-1-{4-[4-(2-pyrimidinyl)-1-piperazinyl]butyl}-1H-pyrazole dihydrochloride, 4-ethoxycarbonyl-1-{4-[4-(2-pyrimidinyl)-1-piperazinyl]butyl}-1H-pyrazole, 3-methyl-5-phenyl-1-{4-[4-(2-pyrimidinyl)-1-piperazinyl]butyl}-1H-pyrazole, 4-bromo-1-{4-[4-(2-pyrimidinyl)-1-piperazinyl]butyl}-1H-pyrazole, 4-cyano-1-{4-[4-(2-pyrimidinyl)-1-piperazinyl]butyl}-1H-pyrazole, 4-fluoro-1-{4-[4-(2-pyrimidinyl)-1-piperazinyl]butyl}-1H-pyrazole, 4-amino-1-{4-[4-(2-pyrimidinyl)-1-piperazinyl] butyl}-1H-pyrazole, 4-methylsulfonamido-1-{4-[4-(2-pyrimidinyl)-1-piperazinyl]butyl}-1H-pyrazole, 4-benzamido-1-{4-[4-(2-pyrimidinyl)-1-piperazinyl]butyl}-1H-pyrazole, 4-acetamido-1-{4-[4-(2-pyrimidinyl)-1-piperazinyl]butyl}-1H-pyrazole, 4-(2-butyl)amino-1-{4-[4-(2-pyrimidinyl)-1-piperazinyl]butyl}-1H-pyrazole, 3-chloro-4-fluoro-1-{4-[4-(2-pyrimidinyl)-1-piperazinyl]butyl}-1H-pyrazole, 4-(4-methoxyphenyl)-1-{4-[4-(2-pyrimidinyl)-1-piperazinyl]butyl}-1H-pyrazole, 4-(4-chlorophenyl)-1-{4-[4-(2-pyrimidinyl)-1-piperazinyl]butyl}-1H-pyrazole, 4-(1-pyrrolyl)-1-{4-[4-(2-pyrimidinyl)-1-piperazinyl]butyl}-1H-pyrazole, 4-phenyl-1-{4-[4-(2-pyrimidinyl)-1-piperazinyl]butyl}-1H-pyrazole, 3,5-diphenyl-1-{4-[4-(2-pyrimidinyl)-1-piperazinyl]butyl}-1H-pyrazole, 4-phenylsulfamoyl-1-{4-[4-(2-pyrimidinyl)-1-piperazinyl]butyl}-1H-pyrazole, 4-{4-methylbenzene)sulfamoyl-1-{4-[4-(2-pyrimidinyl)-1-piperazinyl]butyl}-1H-pyrazole, 4-butylsulfamoyl-1-{4-[4-(2-pyrimidinyl)-1-piperazinyl]butyl}-1H-pyrazole, 4-propylsulfamoyl-1-{4-[4-(2-pyrimidinyl)-1-piperazinyl]butyl}-1H-pyrazole, 4-ethylsulfamoyl-1-{4-[4-(2-pyrimidinyl)-1-piperazinyl]butyl}-1H-pyrazole, 3,5-dimethyl-4-(N,N-dimethylsulfamoyl)-1-{4-[4-(2-pyrimidinyl)- 1-piperazinyl]butyl}-1H-pyrazole, 4-N-methylsulfamoyl-1-{4-[4-(2-pyrimidinyl)-1-piperazinyl]butyl}-1H-pyrazole, 4-sulfo-1-{4-[4-(2-pyrimidinyl)-1-piperazinyl]butyl}-1H-pyrazole, 1-{4-[4-(2-pyrimidinyl)-1-piperazinyl]butyl}-1H-imidazole, 2-methyl-1-{4-[4-(2-pyrimidinyl)-1-piperazinyl]butyl}-1H-imidazole, 4,5-dichloro-1-{4-[4-(2-pyrimidinyl)-1-piperazinyl]butyl}-1H-imidazole, 4-chloro-1-{4-[4-(4-methoxyphenyl)-1-piperazinyl]butyl}-1H-pyrazole, 4,5-dichloro-2-methyl-1-{4-[4-methoxyphenyl)- 1-piperazinyl]butyl}-1H-imidazole, 4-chloro-1-{4-[4-(2-methoxyphenyl)-1-piperazinyl]butyl}-1H-pyrazole, 4,5-dichloro-2-methyl-1-{4-[4-(2-methoxyphenyl)-1-piperazinyl]butyl}-1H-imidazole, 4-chloro-1-{4-[4-(3-methoxyphenyl)-1-piperazinyl]butyl}-1H-pyrazole, 1-{4-[4-(4-methoxyphenyl)-1-piperazinyl]butyl}pyrrole, 1-{4-[4-(2-methoxyphenyl)-1-piperazinyl]butyl}pyrrole, 1-{4-[4-phenyl-1-piperazinyl]butyl}pyrrole, 4-chloro-1-{4-[4-phenyl-1-piperazinyl]butyl}-1H-pyrazole, 4,5-dichloro-2-methyl-1-{4-[4-phenyl-1-piperazinyl]butyl}-1H-imidazole, 4-chloro-1-{4-[4-(2-chlorophenyl)-1-piperazinyl]butyl}-1H-pyrazole, 4,5-dichloro-2-methyl-1-{4-[4-(2-chlorophenyl)-1-piperazinyl]butyl}-1H-imidazole, 4-chloro-1-{4-[4-(3-chlorophenyl)-1-piperazinyl]butyl}-1H-pyrazole, 4,5-dichloro-2-methyl-1-{4-[4-(2-cyanophenyl)-1-piperazinyl]butyl}-1H-imidazole, 4,5-dichloro-2-methyl-1{4-[4-(2-fluorophenyl)-1-piperazinyl]butyl}-1H-imidazole, 4-chloro-1-{4-[4-(2-cyanophenyl)-1-piperazinyl]butyl}-1H-pyrazole, 4,5-dichloro-2-methyl-1-{4-[4-(3-trifluoromethylphenyl)- 1-piperazinyl]butyl}-1H-imidazole, 4-chloro-1-{4-[4-(3-trifluoromethylphenyl)-1-piperazinyl]butyl}-1H-pyrazole, 4-chloro-1-{4-[4-(2-fluorophenyl)-1-piperazinyl]butyl}-1H-pyrazole, 4-chloro-1-{4-[4-(1,2-benzisothiazol-3-yl)-1-piperazinyl]butyl}-1H-pyrazole, 4,5-dichloro-2-methyl-1-{4-[4-(1,2-benzisothiazol-3-yl)-1-piperazinyl]butyl}-1H-imidazole, 1-{4-[4-(1,2-benzisothiazol-3-yl)-1-piperazinyl]butyl}-1H1,2,4-triazole, 1-{4-[4-(1,2-benzisothiazol-3-yl)-1-piperazinyl]butyl}-1H-benzimidazole, 4-bromo-1-{4-[4-(5-bromopyrimidin-2-yl)-1-piperazinyl]butyl}-1H-pyrazole, and 4-bromo-1-{4-[4-(5-chloropyrimidin-2-yl)-1-piperazinyl]butyl}-1H-pyrazole.

3. The method of claim 1 wherein Ar is 2-pyrimidine.

4. The method of claim 3 wherein $Z_1$ is N, $Z_2$ is CH, and $Z_4$ is CH.

5. The method of claim 4 wherein $R_3$ is Cl.

\* \* \* \* \*